United States Patent
Lin et al.

(10) Patent No.: US 9,107,979 B2
(45) Date of Patent: Aug. 18, 2015

(54) BIORESORBABLE POROUS FILM

(71) Applicant: Industrial Technology Research Institute, Hsinchu (TW)

(72) Inventors: Li-Hsin Lin, Hsinchu (TW); Hsin-Hsin Shen, Zhudong Township (TW); Ying-Hsueh Chao, Tainan (TW); Hsiu-Hua Huang, New Taipei (TW); Yu-Bing Liou, Hsinchu (TW); Chih-Bing Hung, Taichung (TW); Chin-Fu Chen, New Taipei (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 118 days.

(21) Appl. No.: 13/870,178

(22) Filed: Apr. 25, 2013

(65) Prior Publication Data
US 2014/0161842 A1 Jun. 12, 2014

(30) Foreign Application Priority Data
Dec. 6, 2012 (TW) .............................. 101145803 A

(51) Int. Cl.
A61K 9/00 (2006.01)
A61L 27/26 (2006.01)
A61L 27/58 (2006.01)
A61L 27/54 (2006.01)
A61L 27/56 (2006.01)
A61K 9/70 (2006.01)

(52) U.S. Cl.
CPC .................. *A61L 27/26* (2013.01); *A61L 27/54* (2013.01); *A61L 27/56* (2013.01); *A61L 27/58* (2013.01); *A61K 9/006* (2013.01); *A61K 9/70* (2013.01); *A61K 9/7007* (2013.01)

(58) Field of Classification Search
None
See application file for complete search history.

(56) References Cited

U.S. PATENT DOCUMENTS

| | | | |
|---|---|---|---|
| 5,855,608 A | 1/1999 | Brekke et al. | |
| 5,935,594 A | 8/1999 | Ringeisen et al. | |
| 5,948,020 A | 9/1999 | Yoon et al. | |
| 6,031,148 A | 2/2000 | Hayes et al. | |
| 6,436,426 B1 | 8/2002 | Liao et al. | |
| 6,579,533 B1 | 6/2003 | Tormala et al. | |
| 6,673,362 B2 | 1/2004 | Calhoun et al. | |
| 6,712,851 B1 | 3/2004 | Lemperle et al. | |
| 6,752,834 B2 | 6/2004 | Geistlich et al. | |
| 6,905,759 B2* | 6/2005 | Topolkaraev et al. | ........ 428/220 |
| 7,704,520 B1 | 4/2010 | Calhoun | |
| 2003/0176876 A1 | 9/2003 | Chen et al. | |
| 2005/0186251 A1 | 8/2005 | Pirhonen et al. | |
| 2008/0057103 A1 | 3/2008 | Roorda | |
| 2010/0034869 A1 | 2/2010 | Tessmar et al. | |
| 2010/0166863 A1 | 7/2010 | Shen et al. | |
| 2012/0027833 A1* | 2/2012 | Zilberman | .................... 424/422 |

FOREIGN PATENT DOCUMENTS

| | | |
|---|---|---|
| TW | I235670 | 4/1992 |
| TW | I323667 | 8/1992 |
| TW | I367100 | 12/1997 |
| TW | I232873 | 5/2005 |
| TW | 201024338 A1 | 7/2010 |
| TW | 201225994 A1 | 7/2012 |

OTHER PUBLICATIONS de Faria et al.,"Preparation and Characterization of Poly(D,L-Lactide) (PLA) and Poly(D,L-Lactide)-Poly(Ethylene Glycol) (PLA-PEG) Nanocapsules Containing Antitumoral Agent Methotrexate", Macromol. Symp., 2005, 229, pp. 228-233.
Farzad et al.,"Guided bone regeneration A literature review", JOHOE, vol. 1, No. 1, 2012, pp. 3-18.
Huang et al.,"Drug release from PLA-PEG microparticulates", International Journal of Pharmaceutics, 156, 1997, pp. 9-15.
Kumari et al., "Biodegradable polymeric nanoparticles based drug delivery systems", Colloids and Surfaces B: Biointerfaces, 75, 2010, pp. 1-18.
Lin et al.,"Guided Tissue Regeneration in Periapical Surgery", JOE, vol. 36, No. 4, Apr. 2010, pp. 618-625.
Lin, "Biodegradable Polymers in Drug Delivery", Presentation by Caiping Lin, Chemical Department, College of Environmental Science and Forestry, State University of New York, Nov. 29, 2005, 30 pages.
Robert et al., "Biocompatibility and resorbability of a polylactic acid membrane for periodontal guided tissue regeneration", Biomaterials, vol. 14, No. 5, 1993, pp. 353-358.
Vila et al.,"Transport of PLA-PEG particles across the nasal mucosa effect of particle size and PEG coating density", Journal of Controlled, Release 98, 2004, pp. 231-244.
Taiwanese Office Action dated Sep. 16, 2014 for Taiwanese Application No. 101145803.

* cited by examiner

*Primary Examiner* — James Rogers
(74) *Attorney, Agent, or Firm* — Birch, Stewart, Kolasch & Birch, LLP

(57) ABSTRACT

A bioresorbable porous film, including a blend mixture of polylactic acid and at least two kinds of polyethylene glycol, wherein the at least two kinds of polyethylene glycol include a first polyethylene glycol, which is in a solid form under ambient temperature and atmospheric pressure, and a second polyethylene glycol, which is in a liquid form under ambient temperature and atmospheric pressure is provided. The film has a porosity of 10%-90%.

11 Claims, 12 Drawing Sheets

BIORESORBABLE POROUS FILM

CROSS REFERENCE TO RELATED APPLICATIONS

This application claims priority of Taiwan Patent Application No. 101145803, filed on Dec. 6, 2012, the entirety of which is incorporated by reference herein.

BACKGROUND

1. Technical Field

The technical field relates to a bioresorbable porous film.

2. Description of the Related Art

In the field of prosthetics, doctors often repair tissues or help tissues to regenerate by guided tissue regeneration; for example, regeneration of the attachment of periodontal ligaments to the bones around periodontal lesion sites. During surgery, a cell-occlusive, liquid-permeable barrier is needed, usually in the form of thin films, which are known as being a semi-permeable film that covers and segregates a bone defect from the surrounding epithelial tissues. The semi-permeable film is used in response to the faster proliferation speed of epithelium than connective tissues. If the semi-permeable film is not used, the epithelium might occupy all of the space where the connective tissues originally grew. Although commercial products of cell occlusive, liquid-permeable films are available, they need to be removed by surgery once the tissues have been regenerated because of the non-bioresorbability of the films. The non-bioresorbability of the films needs an additional surgery and thus causes the patients suffer another period of recovery.

As technology flourishes, there arises a need to provide a bioresorbable carrier with drug delivery and controlled release ability, in order to avoid use of additional drugs like antibiotics or anti-inflammatory medications and additional surgeries. To fulfill the above need, a drug-carrying liquid composition has been proposed. All though the liquid composition may be placed on the treatment site to form a film in situ through solvent volatilization. But however, the solvent votilization also votilizes a considerable amount of the needed drug, thereby reducing the drug content.

In view of the above, there is a need in the art for a bioresorbable, biocompatible film that is able to control drug release with relatively high drug content.

BRIEF SUMMARY

According to one embodiment, a bioresorbable porous film including a blend mixture of polylactic acid and at least two kinds of polyethylene glycol, wherein the at least two kinds of polyethylene glycol comprise a first polyethylene glycol, which is in a solid form under ambient temperature and atmospheric pressure, and a second polyethylene glycol, which is in a liquid form under ambient temperature and atmospheric pressure, is provided. The film has a porosity of 10%-90%.

A detailed description is given in the following embodiments with reference to the accompanying drawings.

BRIEF DESCRIPTION OF THE DRAWINGS

The embodiments can be more fully understood by reading the subsequent detailed description and examples with references made to the accompanying drawings, wherein.

DETAILED DESCRIPTION

Figure 1:
FIG. 1 is an image of a failed sample according to Comparative Example 1.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The disclosure provides a composite film formed from a blend mixture of polylactic acid and at least two kinds of polyethylene glycol of different physical states. The aforementioned two kinds of polyethylene glycol include a first polyethylene glycol, which is in a solid form under ambient temperature and atmospheric pressure, and a second polyethylene glycol, which is in a liquid form under ambient temperature and atmospheric pressure. In one embodiment, the first polyethylene glycol has a weight-average molecular weight in a range of 2000-10,000, and the second polyethylene glycol has a weight-average molecular weight in a range of 300-600, and the polylactic acid has a weight-average molecular weight in a range of 50,000-400,000. In one embodiment, the three may be blended by the weight ratio according to Formula (I), $$PLAx/PEG(2000\text{-}10{,}000)y/PEG(300\text{-}600)z$$

$$x+y+z=100, x=30\text{-}80, y+z=70\text{-}20. \tag{I}$$

wherein the y is between 50-10, and the z is between 50-10. In addition, a solvent may be added while blending, e.g. tetrahydrofuran (THF), $CHCl_2$, or combinations thereof, to prepare a 20 wt %-40 wt % solution, and 1 wt %-20 wt % of a drug may also be optionally added. The aforementioned solution may be heated and stirred to completely dissolve the solid content and then coated on a substrate (e.g. glass, plastic, metal or other suitable materials), for example, by an automatic coating machine or other suitable coating methods. A flat film of 10 μm-200 μm in thickness (variation ±5 μm) may thus be obtained after removing the solvent by a suitable drying process. In one embodiment, the drying process may include, but are not limited to, air drying, oven drying (40° C.-50° C.), and vacuum drying. The bioresorbable porous film may be disposed within or onto mammalian tissues, or other suitable locations.

Polylactic acid (PLA) and polyethylene glycerol (PEG) are both bioresorbable, biocompatible, and translucent, which have long been clinically used. These two compounds are hypoallergenic and capable of releasing drug content contained therein in a controlled manner so as to suppress pain and inflammation of lesion sites. In one embodiment, the film may be self-absorbed completely without any possible toxic or residual left in the body after 3 months to 1 year, which varies according to the thickness of the film.

The PLA used in the embodiments may be a polymer or a copolymer of L-lactic acid unit, D-lactic acid unit, and/or other suitable monomers, but D,L-polylactic acid (PDLLA) formed of D-lactic acid and L-lactic acid is particularly preferred. This kind of PLA has less crystallinity, with a melting point ranging between 150° C.-190° C. The weight-average molecular weight of PLA may be in a range of 50,000-400,000, for example, about 130,000. The inherent viscosity of the PLA may be between 1.6 dl/g-2.4 dl/g.

The two kinds of PEG used in the embodiments have two physical states at room temperature, due their two different intervals of molecular weight regions. A PEG with a lower molecular weight (300-600, e.g., 300-500) may appear as a tacky viscous liquid and possess hygroscopicity and a wide range of chemical compatibility, which means that the PEG may dissolve most materials stably without interacting with the materials. A PEG with a higher molecular weight (2000-10000, e.g. 6000-9000) may be in a solid form at room temperature and ambient pressure, and have good crystallinity and better ability for forming porous.

Using the two PEGs of two molecular weight regions can make the PLA film porous, wherein the solid PEG (first PEG) may capsulate the liquid, drug-containing PEG (second PEG) so as to maintain the drug content and keep the film shape. By tuning the composition ratio of the three components, the amount and the size of the pores may be adjusted according to the drug contained therein. Since the solvent volatilizes into the atmosphere when dried, the first surface of the bioresorbable porous film that faces the substrate may possess more and larger pores while the second surface that faces the atmosphere may possess less and smaller pores. In practice, the first surface with larger porous may be in contact with the lesion site in order to accelerate the diffusion of the contained drug. In a preferred embodiment, the pore diameter may be in a range of 0.2 μm-3 μm.

In one embodiment, the film may include hydrophilic drugs, hydrophobic drugs, growth factors, bioactive agents, or combinations, for example, aspirin, lidocaine, chloramphenicol, ibuprofen, fenbufen, diclofenac sodium, insulin-like growth factors, epithermal growth factors, platelet-derived growth factors, and/or other suitable compositions.

In some embodiments, the amount and the size of the pores may be affected by the composition ratio of the materials and the properties of the drug contained in the film. A higher PLA content and/or a hydrophobic drug leads to smaller and fewer pores. The size and the amount of the pores may further affect the release rate of the drug. The greater amount of pores and/or the larger the pores, the higher the drug release ratio. In the absence of the pores, the drug release ratio would be far less and limited, since the surface effusion is the only route for drug release. The drug release ratio is defined as follows:

$$\text{drug release ratio} = \frac{\text{amount of drug released}(g)}{\text{amount of drug loading}(g)} \times 100\%$$

It should be noted that the amount and the size of the pores is tunable according to the aforementioned properties, but once the composition ratio of a solution is out of the range defined by Formula (I), the solution may not be able to form a film. For example, when the ratio of PLA, x, is above 80 (that is, the PLA content is too high), the film may be brittle, inelastic, and easily broken when pulled. On the other hand, when x is below 30, the PLA may not be able to encapsulate the overloaded PEG molecules and cause crystallization of PEG, thus failing to form a film.

Moreover, the two PEGs with different physical properties are both indispensable. For example, a formulation composed of only the PLA and PEG (2000-10000, and the first PEG, without the second PEG (300-600) would result in different degrees of crystallizations over the entire film, making the film uneven and inelastic. On the other hand, when a PEG having a molecular weight higher than 10000 is used, local crystallization was observed, even if a liquid PEG is incorporated, thus adversely affecting integrity and utility of a film. Furthermore, in the absence of the solid PEG (only PLA and liquid PEG), the ratio of PLA may reach above 40 wt % to form a film, and the liquid PEG would outflow from the film due to the lack of encapsulation of the solid PEG.

The disclosure provides a porous composite film which may be used in guided tissue regeneration treatment, and the film may optionally contain a drug (drug content up to 20 wt %) and the drug may be released in a controlled manner. The film prepared according to the composition ratio provided in the embodiments is capable of tuning the amount and size of the pores and may reach at least 75% of a drug release ratio. PLA and PEG are biocompatible, and bioresorbable, which means the film may be self-absorbed after a period of time, non-toxic, and hypoallergenic. No surgery is required to retrieve the film after tissue regeneration. The disclosed film may be useful for implantation into or disposal onto the mammalian tissue in order to effectively assist in the treatment progress, for example, periodontal disease treatment, prosthetic treatment after extraction or missing tooth trauma, or the like.

EXAMPLE & COMPARATIVE EXAMPLE

TABLE 1

|   | composition ratio (%) | drug/drug content | drug release rate | porosity |
|---|---|---|---|---|
| EXAMPLE 1 | PLA/PEG(6000)/PEG(300) = 30/35/35 | | | 90.80% |
| EXAMPLE 2 | PLA/PEG(6000)/PEG(300) = 50/25/25 | | | 82.30% |
| EXAMPLE 3 | PLA/PEG(6000)/PEG(300) = 50/25/25 | Lidocaine/20% | >80% | |
| EXAMPLE 4 | PLA/PEG(6000)/PEG(300) = 50/25/25 | Chloramphenicol/20% | >75% | |
| EXAMPLE 5 | PLA/PEG(6000)/PEG(300) = 70/15/15 | | | 58.40% |
| EXAMPLE 6 | PLA/PEG(6000)/PEG(300) = 70/15/15 | Lidocaine/20% | >80% | |
| EXAMPLE 7 | PLA/PEG(6000)/PEG(300) = 80/10/10 | | | 21.60% |
| C. EXAMPLE 1 | PLA/PEG(6000)/PEG(300) = 20/40/40 | | | no film formed |
| C. EXAMPLE 2 | PLA/PEG(6000)/PEG(300) = 100/0/0 | | | 0% |
| C. EXAMPLE 3 | PLA/PEG(6000)/PEG(300) = 100/0/0 | Lidocaine/20% | ≤40% | |
| C. EXAMPLE 4 | PLA/PEG(6000)/PEG(300) = 50/50/0 | | | no film formed |

TABLE 1-continued

| | composition ratio (%) | drug/drug content | drug release rate | porosity |
|---|---|---|---|---|
| C. EXAMPLE 5 | PLA/PEG(8000)/ PEG(300) = 20/40/40 | | | no film formed |
| C. EXAMPLE 6 | PLA/PEG(8000)/ PEG(300) = 50/50/0 | | | no film formed |
| C. EXAMPLE 7 | PLA/PEG(10000)/ PEG(300) = 40/60/0 | | | no film formed |
| C. EXAMPLE 8 | PLA/PEG(10000)/ PEG(300) = 50/25/25 | | | local crystallization |

Each example and comparative example was carried out by blending the PLA (15 g) and two PEGs (15 g) with different molecular weight regions according to Table 1. Then the blend mixture was dissolved into tetrahydrofuran (THF 70 g) as a 30 wt % solution. Optionally, 7.5 g of a hydrophilic drug Lidocaine (Example 3, 6 and Comparative Example 3) or hydrophobic drug Chloramphenicol (Example 4) was added. Then the solution was stirred thoroughly and heated to react with a drug content of 20 wt %, and the solution was applied on a glass substrate by an auto coating machine (ZAA-2300; Zehntner GmbH Testing Instruments) and dried overnight to form a porous film of 100±5 μm. The film structure and the pore configuration were observed with a scanning electron microscope (magnified 10000 folds) (QUANTA-400F, FEI-PHILIPS) and mercury porosimeter (SCIENTEK CORPORATION). Additionally, a control-release experiment was performed under 37° C. by an aqueous system using PBS.

Figure 2:
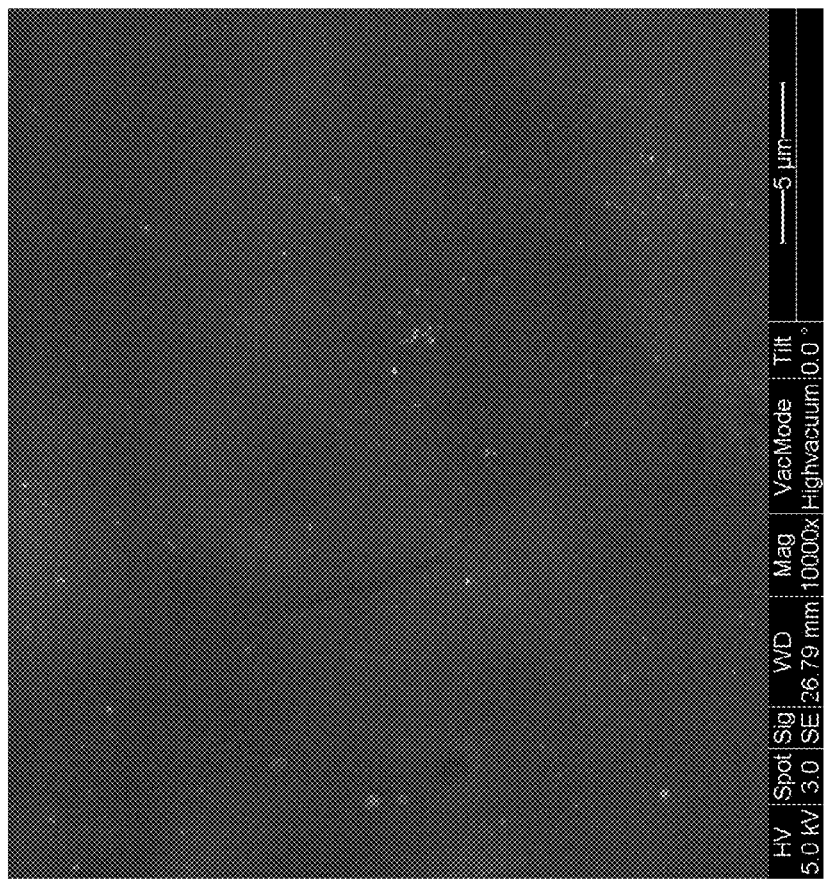
FIG. 2 is a SEM (scanning electron microscope) image of the film surface of Comparative Example 2 (magnified 10000 fold)

In Examples 1, 2, 5 and 7 and Comparative Examples 1 and 2, the correlation between the proportion of solutions and the porosity was observed. FIG. 1 shows the sample of Comparative Example 1, wherein a solution with 20 wt % of PLA was unable to encapsulate the PEG and caused PEG crystallization, failing to form a film. FIG. 2 shows the sample of Comparative Example 2, wherein a solution of 100 wt % PLA resulted in a non-porous film. As shown in FIG. 2 (magnified 10000 folds), no pore was observed, and the porosity was nearly 0%.

Figure 3A:
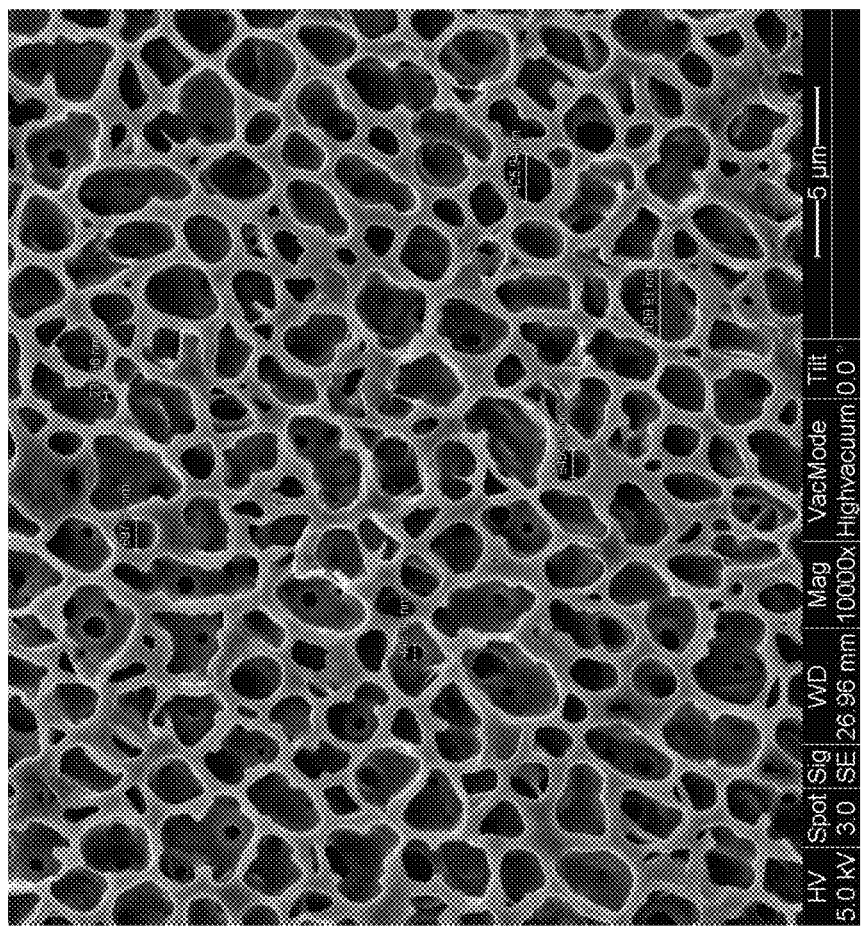
FIG. 3A-3B are respectively the top view and the cross-sectional view of the film with 20 wt % hydrophilic Lidocaine in Example 3 (magnified 10000 fold)
Figure 3B:
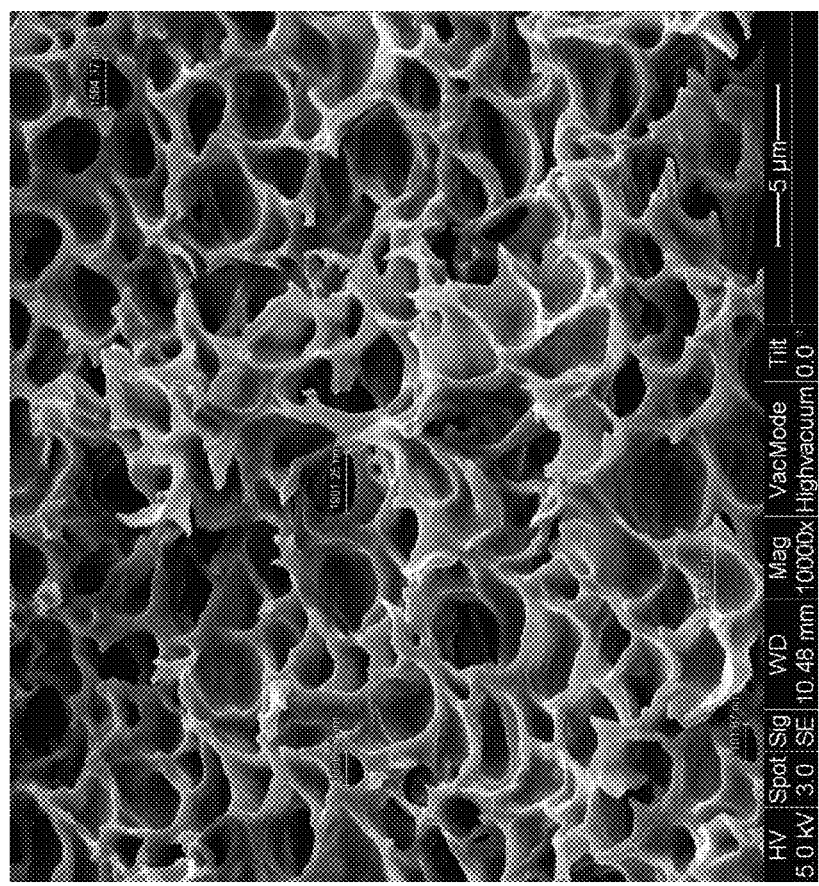
Figure 4A:
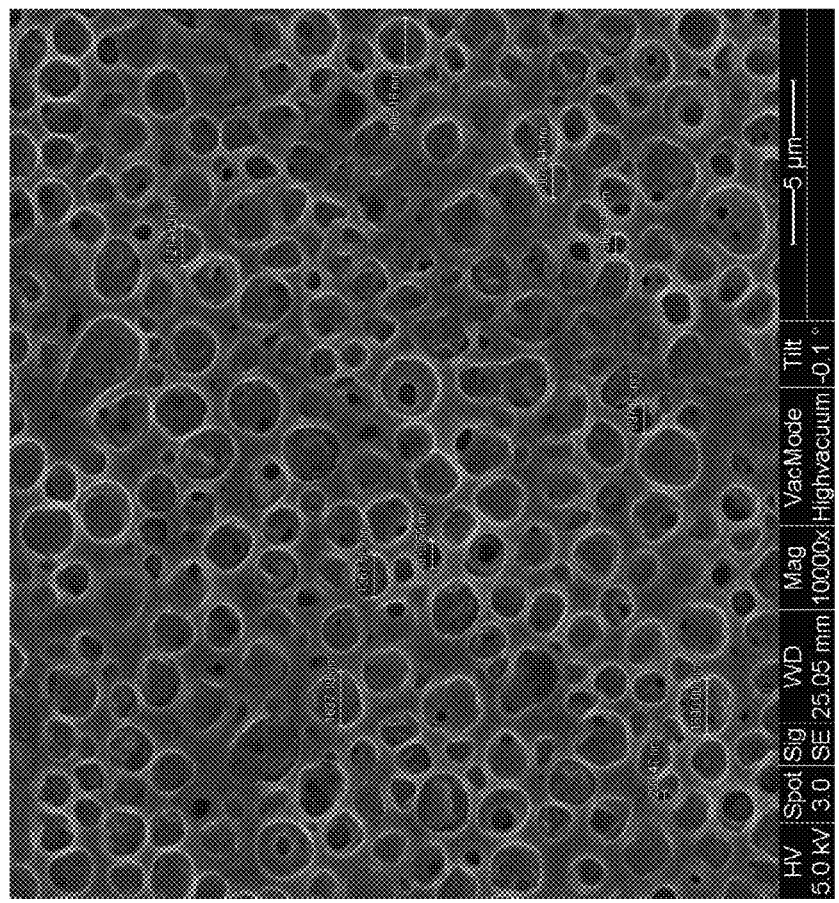
FIG. 4A-4B are respectively the top view and the cross-sectional view of the film with 20 wt % hydrophobic Chloramphenicol in Example 3 (magnified 10000 fold)
Figure 4B:
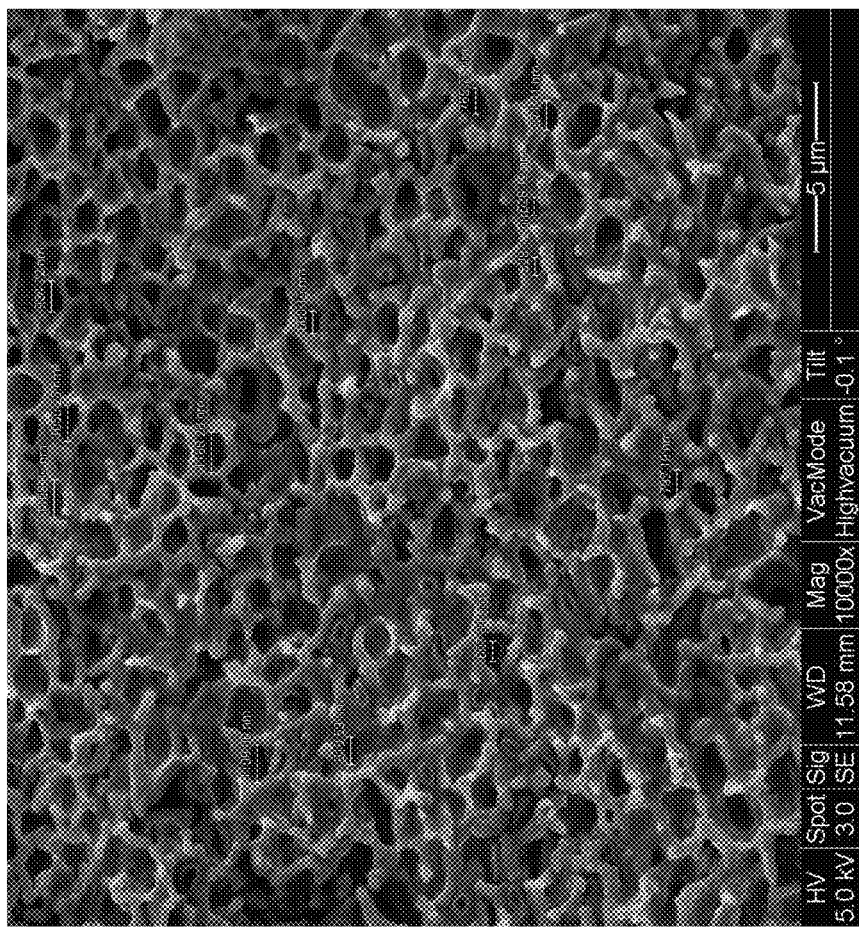
Figure 5A:
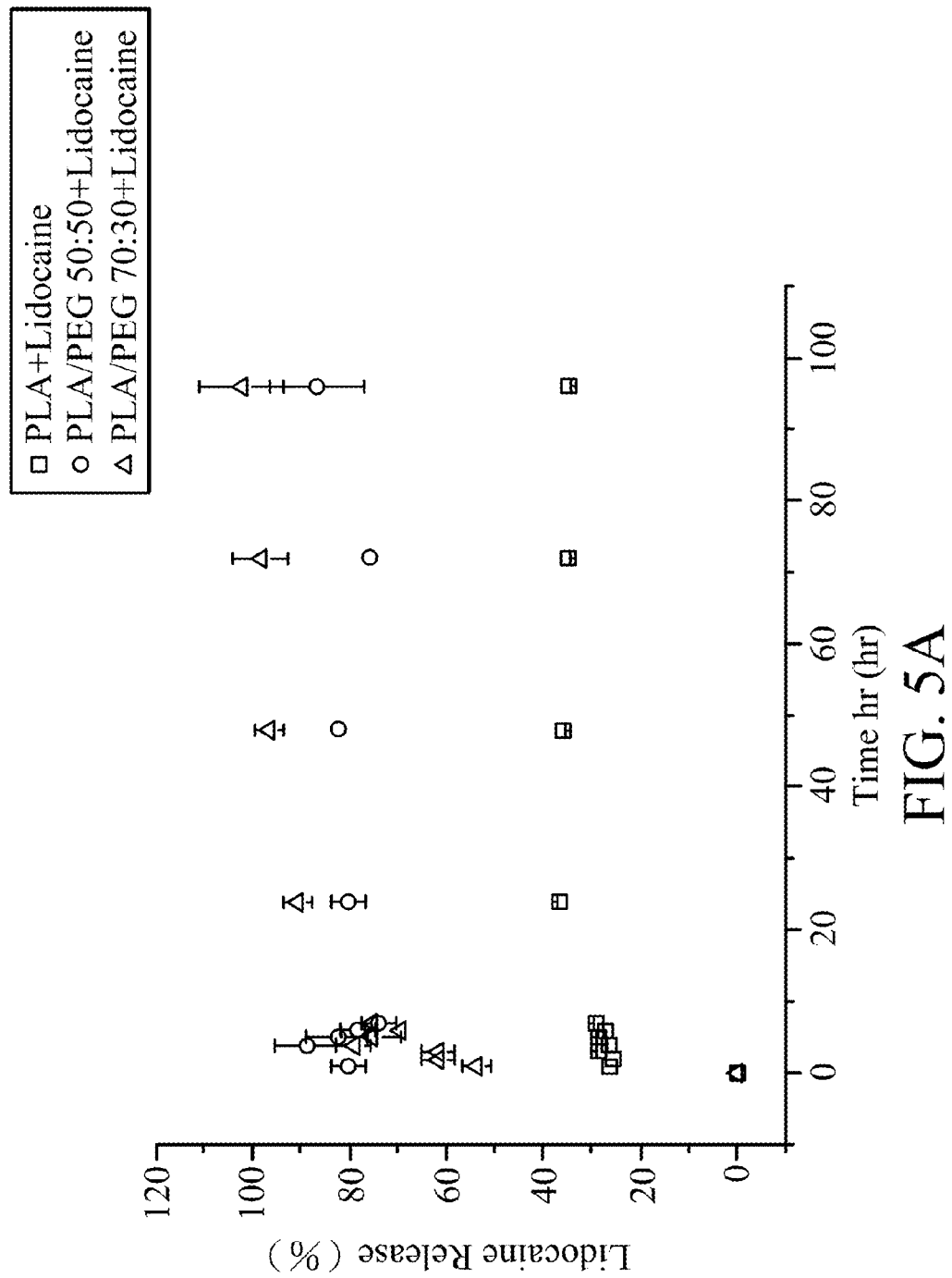
FIG. 5A-5B are diagrams showing the drug release status of the films of the Example 3, 4 and 6 and Comparative Example 3 in a time scale.
Figure 5B:
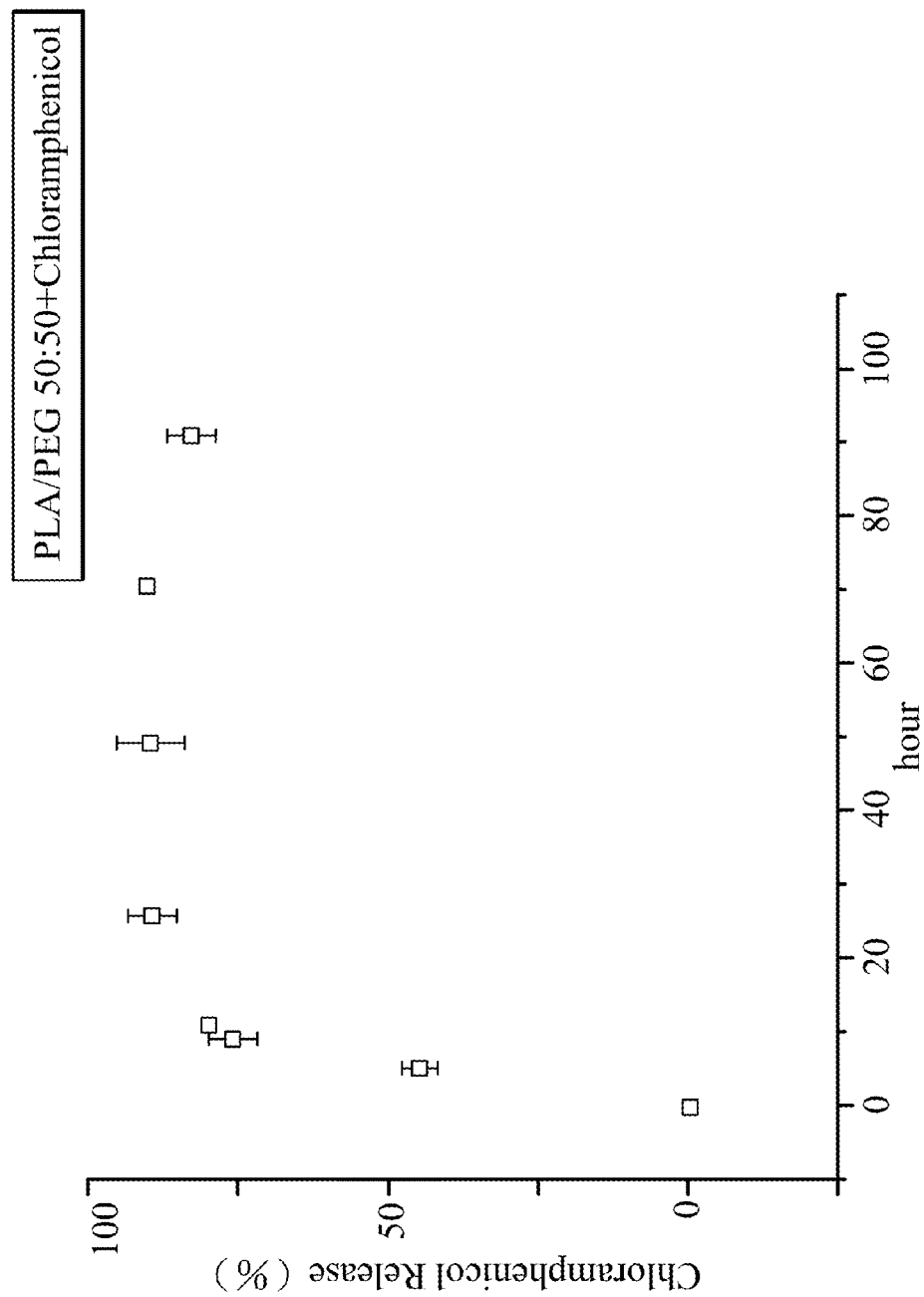

FIGS. 3A and 3B respectively show the top view and the cross-sectional view of the film with 20 wt % hydrophilic Lidocaine in Example 3. FIGS. 4A and 4B, respectively, show a top view and a cross-sectional view of the film with 20 wt % hydrophobic Chloramphenicol in Example 4. It can be observed that with the film containing hydrophilic drugs, the amount and the size of the pores were greater and larger than the one containing hydrophobic drugs. Also, FIGS. 5A and 5B show that the drug release ratio (>80%) of the hydrophilic drug was higher than the drug release rate (~75%) of the hydrophobic drug, which indicated a correlation between the drug release ratio and pore configuration. Moreover, the drug release ratios of the porous film of the Examples were significantly higher than that of Comparative Example 1 (75% v.s. 40%).

Figure 6A:
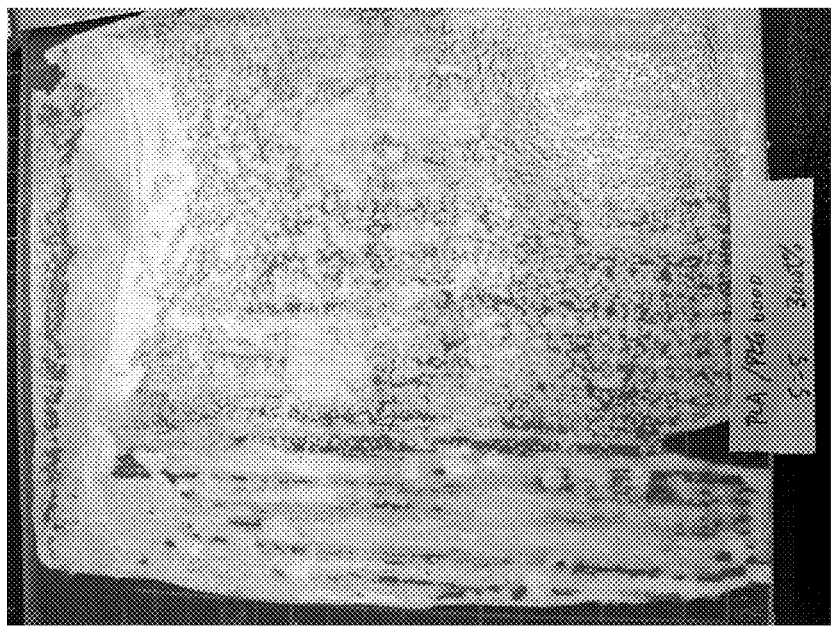
FIGS. 6A-6C and 7 are sample images of Comparative Example 4 and 6-8.
Figure 6B:
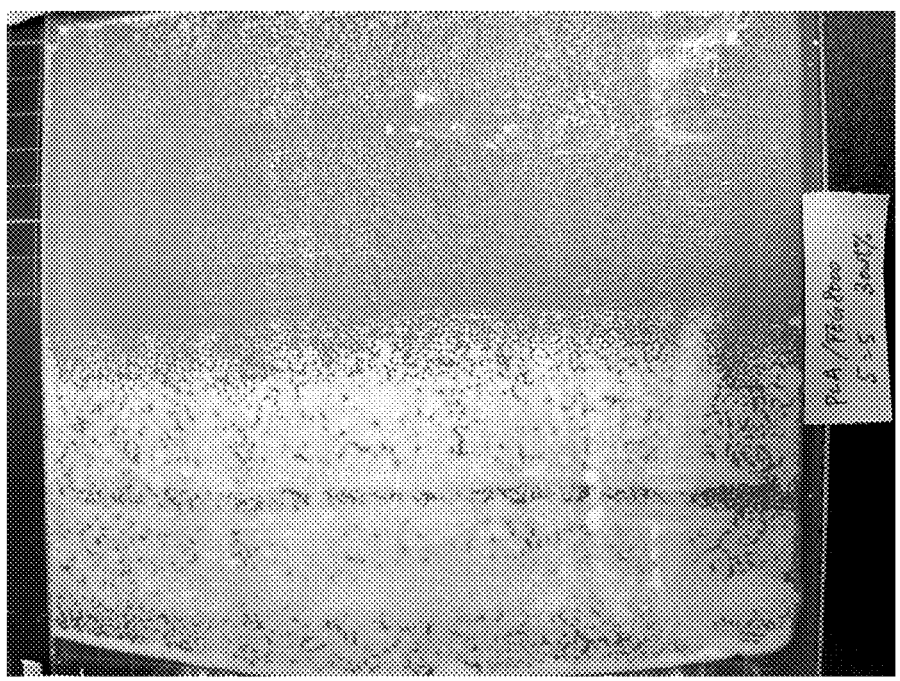
Figure 6C:
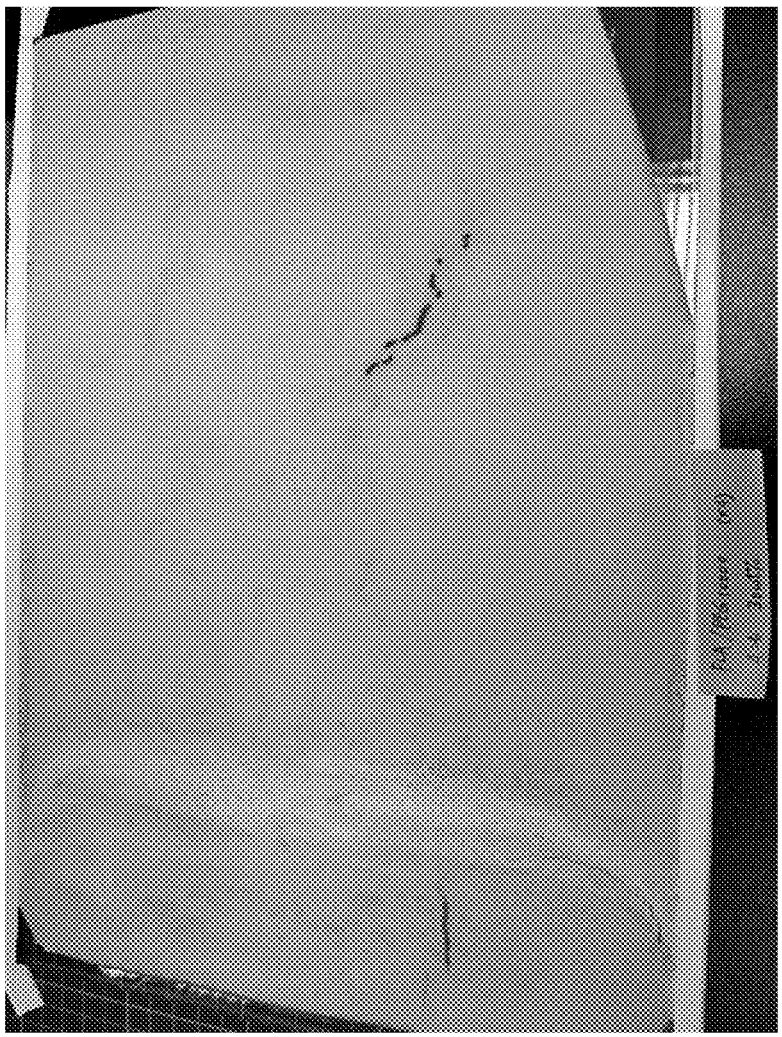

FIG. 6A-6C show the samples of Comparative Examples 4, 6 and 7, which were the films without the liquid form of PEG (second PEG). Specifically, only PLA and the solid form of PEG (first PEG of molecular weight 6000-10000) existed in the films. It was seen that there were varying degrees of crystallization occurring in the films, which caused the film to become uneven and inelastic.

Figure 7:
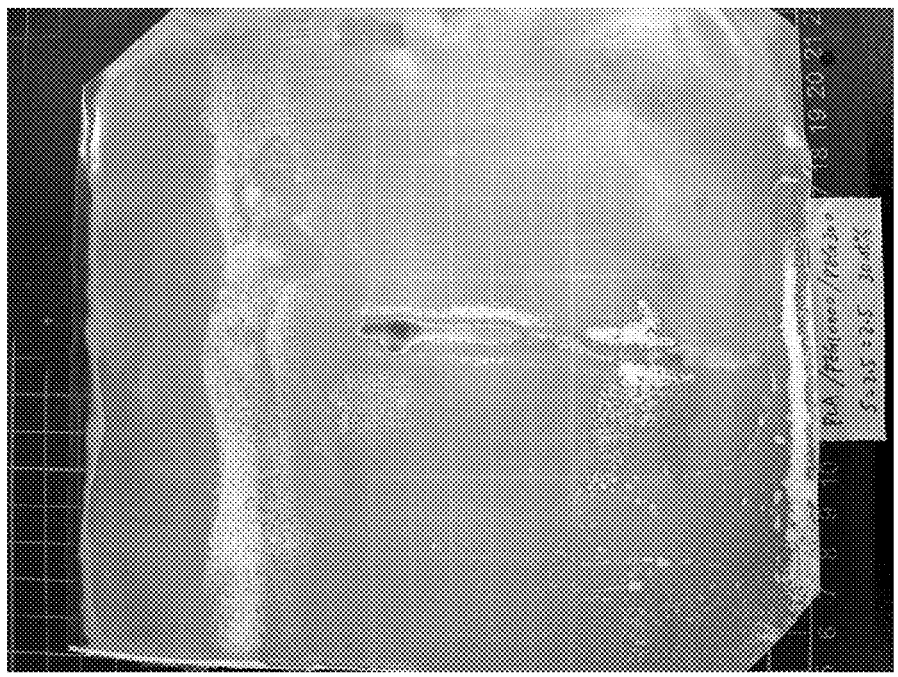

In addition, FIG. 7 shows the sample of Comparative Example 8, which was a result after adding PEG with its molecular weight close to the maximum limit. The film kept most of the characteristics as a film (such as elasticity and tenacity), but it was also observed that there were some occurrences of subtle crystallizations.

Various changes, substitutions and alterations can be made herein without departing from the spirit and scope of the embodiments as defined by the appended claims, as one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the disclosure. Accordingly, the appended claims are intended to include within their scope such processes, machines, manufacture, compositions of matter, means, methods, or steps. In addition, each claim constitutes a separate embodiment, and the combination of various claims and embodiments are within the scope of the disclosure.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A bioresorbable porous film, comprising:
   a blend mixture of polylactic acid and at least two kinds of polyethylene glycol;
   wherein the at least two kinds of polyethylene glycol comprise a first polyethylene glycol, which is in a solid form under ambient temperature and atmospheric pressure, and a second polyethylene glycol, which is in a liquid form under ambient temperature and atmospheric pressure;
   wherein the first polyethylene glycol has a molecular weight in a range of 6000-9000 Da (PEG(6000-9000)), and the second polyethylene glycol has a molecular weight in a range of 300-600 Da (PEG(300-600));
   wherein the film is prepared by a blend mixture according to weight ratio of Formula (I), $$x/y/z$$

$$x+y+z=100\%, x=30\text{-}70\%, y+z=70\text{-}30\%, \quad \text{(I)}$$

wherein x, y, and z represent the weight percentages of PLA, PEG(6000-9000), and PEG(300-600), respectively; and
   wherein the film has a porosity of 58.40%-90.80%.

2. The bioresorbable porous film as claimed in claim 1, wherein the y is between 50-10, and the z is between 50-10.

3. The bioresorbable porous film as claimed in claim 1, wherein the polylactic acid has a molecular weight in a range of 50,000-400,000 Da.

4. The bioresorbable porous film as claimed in claim 1, further comprising bioactive agents.

5. The bioresorbable porous film as claimed in claim 4, wherein the film has at least about 1wt % of drug content.

6. The bioresorbable porous film as claimed in claim 1, wherein the film has a thickness of about 10 μm-200 μm.

7. The bioresorbable porous film as claimed in claim 1, wherein the film has a first surface and a second surface opposite to the first surface, and the first surface has a greater porosity than the second surface.

8. The bioresorbable porous film as claimed in claim 1, wherein the film has pores of 0.2 µm-3 µm in diameter.

9. The bioresorbable porous film as claimed in claim 1, wherein the film is useful for implantation into mammalian tissues or disposal on the mammalian tissues.

10. The bioresorbable porous film as claimed in claim 1, further comprising hydrophilic drugs, hydrophobic drugs or combinations thereof.

11. The bioresorbable porous film as claimed in claim 1, further comprising growth factors.

* * * * *